United States Patent
Gross et al.

(10) Patent No.: US 10,449,089 B2
(45) Date of Patent: *Oct. 22, 2019

(54) APPLICATION OF BLEND ZONES, DEPTH REDUCTION, AND TRANSITION ZONES TO ABLATION SHAPES

(75) Inventors: Erik Gross, Palo Alto, CA (US); Rich Hofer, Santa Cruz, CA (US); Jonathan Wong, Santa Clara, CA (US)

(73) Assignee: AMO MANUFACTURING USA, LLC, Santa Ana, CA (US)

(*) Notice: Subject to any disclaimer, the term of this patent is extended or adjusted under 35 U.S.C. 154(b) by 815 days.

This patent is subject to a terminal disclaimer.

(21) Appl. No.: 13/539,605

(22) Filed: Jul. 2, 2012

(65) Prior Publication Data
US 2012/0271287 A1    Oct. 25, 2012

Related U.S. Application Data

(63) Continuation of application No. 10/100,231, filed on Mar. 14, 2002, now Pat. No. 8,216,213.

(51) Int. Cl.
A61F 9/008    (2006.01)

(52) U.S. Cl.
CPC .......... *A61F 9/008* (2013.01); *A61F 9/00806* (2013.01); *A61F 9/00808* (2013.01); *A61F 9/00817* (2013.01); *A61F 2009/0088* (2013.01); *A61F 2009/00844* (2013.01); *A61F 2009/00846* (2013.01); *A61F 2009/00848* (2013.01); *A61F 2009/00872* (2013.01)

(58) Field of Classification Search
CPC .. A61F 9/008; A61F 9/00806; A61F 9/00808; A61F 9/00817; A61F 2009/00842; A61F 2009/00844; A61F 2009/00846; A61F 2009/00872

USPC ................................. 606/5, 10–13
See application file for complete search history.

(56) References Cited

U.S. PATENT DOCUMENTS

| 4,729,372 A | 3/1988 | L'Esperance, Jr. |
| 4,732,148 A | 3/1988 | L'Esperance, Jr. |
| 5,219,344 A | 6/1993 | Yoder, Jr. |

(Continued)

FOREIGN PATENT DOCUMENTS

| CA | 2478418 | 1/2011 |
| DE | 4337842 A1 | 5/1994 |

(Continued)

OTHER PUBLICATIONS

European Supplementary Search Report dated Oct. 12, 2010, Application No. 03711592.0, 5 pages.
International Search Report of PCT/US03/07903, dated Oct. 28, 2003, 3 pages.
Baron, W., et al, "Predicting Visual Performance Following Excimer Photorefractive Keratectomy," Refractive & Corneal Surgery, 1992, vol. 2, 9 pages.
Author Unknown, "FDA-Approved lasers for PRK and other refractive surgeries," No date, [Retrieved on Jun. 12, 2002], 1 page. Retrieved from: http://www.fda.gov/cdrh/lasik/lasers/htm.

(Continued)

*Primary Examiner* — Lynsey C Eiseman
*Assistant Examiner* — Jessandra F Hough
(74) *Attorney, Agent, or Firm* — Johnson & Johnson Surgical Vision, Inc.

(57) ABSTRACT

Methods, devices, and systems for reprofiling a surface of a cornea of an eye ablate a portion of the cornea to create an ablation zone with an optically correct central optical zone disposed in a central portion of the cornea, and a blend zone disposed peripherally to the central optical zone and at least partially within an optical zone of the eye. The blend zone can have an optical power that gradually diminishes with increasing radius from the central optical zone.

18 Claims, 10 Drawing Sheets

(56) References Cited

U.S. PATENT DOCUMENTS

| | | | |
|---|---|---|---|
| 5,445,633 | A | 8/1995 | Nakamura et al. |
| 5,490,849 | A * | 2/1996 | Smith .............................. 606/5 |
| 5,571,107 | A * | 11/1996 | Shaibani et al. ................. 606/4 |
| 5,683,379 | A * | 11/1997 | Hohla .............................. 606/5 |
| 5,713,892 | A | 2/1998 | Shimmick |
| 5,891,131 | A * | 4/1999 | Rajan et al. ..................... 606/5 |
| 6,090,100 | A | 7/2000 | Hohla |
| 6,190,375 | B1 * | 2/2001 | Frey ................................. 606/5 |
| 6,203,539 | B1 | 3/2001 | Shimmick et al. |
| 6,280,435 | B1 * | 8/2001 | Odrich et al. ................... 606/5 |
| 6,474,814 | B1 * | 11/2002 | Griffin ..................... A61F 2/16 351/161 |
| 8,216,213 | B2 | 7/2012 | Gross et al. |
| 2001/0041884 | A1 | 11/2001 | Frey et al. |
| 2003/0176855 | A1 | 9/2003 | Gross et al. |

FOREIGN PATENT DOCUMENTS

| | | |
|---|---|---|
| EP | 0714646 A1 | 6/1996 |
| EP | 1 482 884 A2 | 12/2004 |
| JP | 2006-505297 A | 2/2006 |
| MX | PA04008924 A | 11/2004 |
| WO | 1991/11158 A1 | 8/1991 |
| WO | 1996/021407 A1 | 7/1996 |
| WO | 1997/014382 A1 | 4/1997 |
| WO | 1998/41178 A1 | 9/1998 |
| WO | 03/077795 A2 | 9/2003 |

OTHER PUBLICATIONS

Garcia, D., et al, "CWhatUC: A Visual Acuity Simulator," Proceedings of SPIE, Ophthalmic Technologies VIII, 1998, vol. 3246, 9 pages.

L'Esperance, F., et al., "Excimer Laser Instrumentation and Technique for Human Corneal Surgery," Archives of Ophthalmology, 1989, vol. 107, 10 pages.

McDonnell, P., et al, "Photorefractive Keratectomy to Create Toric Ablations for Correction of Astigmatism," Archives of Ophthalmology, 1991, vol. 109, 5 pages.

Munnerlyn, C. et al, "Photorefractive keratectomy. A technique for laser refractive surgery." Journal of Cataract & Refractive Surgery, 1986, vol. 14, 8 pages.

Salmon, T., "Chapter 3: Corneal Topography Basics," *Corneal Contribution to the Wavefront Aberration of the Eye*, Ph.D. Dissertation-Electronic Version, 1999, 27 pages. Retrieved from: http://arapaho.nsuok.edu/~salmonto/articles_resources_pdf/Dissertation.html.

Japanese Patent Application H4-322387 (dated Nov. 7, 1992) to Nidek Co., 19 pages.

Japanese Patent Application H4-337929 (dated Nov. 24, 1992) to Nidek Co., 26 pages.

Author Unknown, "VISX Receives FDA Approval for Variable Spot Scanning (VSS) Allowing Larger Treatment Zones," 2001, [Retrieved on Jun. 12, 2002], 2 pages. Retrieved from: http://www.visx.com/whats/press_release1.php.

\* cited by examiner

APPLICATION OF BLEND ZONES, DEPTH REDUCTION, AND TRANSITION ZONES TO ABLATION SHAPES

CROSS-REFERENCES TO RELATED APPLICATIONS

This application is a continuation of U.S. patent application Ser. No. 10/100,231 filed Mar. 14, 2002, entitled "APPLICATION OF BLEND ZONES, DEPTH REDUCTION AND TRANSITION TO ZONES TO ABLATION SHAPES," which is incorporated herein by reference for all purposes.

STATEMENT AS TO RIGHTS TO INVENTIONS MADE UNDER FEDERALLY SPONSORED RESEARCH OR DEVELOPMENT

Not applicable

REFERENCE TO A "SEQUENCE LISTING," A TABLE, OR A COMPUTER PROGRAM LISTING APPENDIX SUBMITTED ON A COMPACT DISK

Not applicable

BACKGROUND OF THE INVENTION

This invention generally relates to laser eye surgery, and in particular provides methods, devices, and systems for selectively ablating corneal tissue to improve the vision of patients having corneal irregularities or other vision defects.

There are known laser-based systems and methods for enabling ophthalmic surgery on the cornea in order to treat vision defects. Typically, these systems and methods perform a process known as ablative photodecomposition, which involves selectively exposing the cornea to laser radiation to remove a microscopic layer of stromal tissue from the cornea. This ablation leads to a resculpting of the cornea, without causing significant thermal damage to adjacent and underlying tissues of the eye. Corneal shaping is intended to change the optical properties of an eye, and thus treat optical defects such as refractive errors. Such shaping is often performed in stromal tissue of the cornea, while a flap of overlying tissue is temporarily displaced in a procedure known as Laser In Situ, Keratomileusis (LASIK).

The distribution of ablation energy across the cornea can be controlled by a variety of systems and methods, including ablatable masks, fixed and moveable apertures, controlled scanning systems, and the like. Optionally, eye movement tracking mechanisms may also be used to control the distribution of ablation energy across the cornea. In known systems, the laser beam often comprises a series of discrete pulses of laser light energy, with the total shape and amount of tissue removed being determined by factors such as, for example, the shape, size, location, or number of laser energy pulses impinging on the cornea. A variety of software and hardware combinations may be used to generate the pattern of laser pulses that reshape the cornea. Methods and systems may provide various forms of lasers and laser energies to effect the treatment, including, for instance, infrared lasers, ultraviolet lasers, femtosecond lasers, wavelength multiplied solid-state lasers, and the like.

By using laser eye surgery to change the shape of the cornea, a broad range of vision defects, including myopia (nearsightedness), hyperopia (farsightedness), and symmetrical cylindrical astigmatisms, are now being treated. Many patients suffer from optical defects that are not easily treated using known corneal reshaping ablation techniques, and in certain circumstances it may not be possible or desirable to follow known ablation profiles. For example, in patients needing very high power corrections, as well as in patients having a particularly large pupil, the depth of tissue that must be removed using current ablation profiles may be greater than that which is considered safe.

Standard ablation profiles may also be inappropriate for a patient having an unusually thin cornea. In these case, there is a need for providing an ablation profile having a reduced ablation depth that still results in useful treatment of the optical defect. Belatedly, there are circumstances where standard ablation profiles may be inappropriate for a patient as known shapes may introduce or amplify night glare problems. Likewise, certain currently used ablation profiles may complicate flap repositioning procedures. What is more, standard ablation profiles can give rise to ablation zones that have abrupt transitions between the treated and untreated portions of the cornea, for example when the depth of an ablation profile does not smoothly transition to zero at the edge of the ablation.

In light of the above, it would be desirable to provide improved optical ablation systems and methods, particularly for use in patients needing high power corrections, in patients having large pupils, or in patients presenting other optical characteristics that render them difficult to treat with current approaches.

BRIEF SUMMARY OF THE INVENTION

The present invention provides improved laser-based methods and systems for correction of vision defects. These systems and methods may be particularly useful for treating patients presenting certain anatomical features, such as large pupil diameters or thin corneal tissue. Advantageously, these techniques generally avoid abrupt changes in ablation depth of the ablation profile, and particularly toward the peripheral areas of the ablation. The form of the ablation profile can vary, depending in part on the type of refractive treatment being administered. The systems and methods of the present invention also are advantageous because they provide ablation zones having decreased angles at the ablation edge; they may reduce incidence of night vision problems, and they may enhance flap positioning and fit in a LASIK procedure. The present invention may be used to treat a wide variety of optical conditions, including, but not limited to, myopia, hyperopia, presbyopia, astigmatism, and irregular astigmatism. To achieve these advantages, the present invention often provides for the incorporation of depth reduction, blend region, and transition region features into treatment ablation profiles to more efficiently and effectively help patients who have heretofore been particularly difficult and/or impossible to treat with conventional techniques.

In a first aspect, a preferred embodiment of the present invention provides a method of reprofiling a cornea of an eye by ablating a portion of the cornea to create an ablation zone. The ablation zone includes an optical zone having an optically correct central optical zone located in a central portion of the cornea, and a blend zone disposed peripherally to the central optical zone and at least partially within an optical zone of the eye, wherein the blend zone has an optical power that gradually diminishes with increasing radius from the central optical zone.

Optionally, the area of the optical zone is equal to a maximum possible pupil size of the eye. The blend zone may have an optical power that diminishes as a linear or nonlinear function of increasing radius. The blend zone can have an optical power that diminishes as a linear or nonlinear monotonic function of increasing radius, the blend zone terminating at an ablation zone edge.

The ablation zone may further comprise a transition zone disposed peripherally to the blend zone, the transition zone being defined by a set of radially oriented cubic splines. The shape of the surface of the cornea can be reprofiled from an initial shape to a shape that mitigates myopia. The shape of the surface of the cornea can also be reprofiled from an initial shape to a shape that mitigates hyperopia, presbyopia, astigmatism, or irregular astigmatism. Optionally, the dimension across the central optical zone may be from about 6 mm to about 7 mm or from about 3 mm to about 9 mm, and/or the dimension across the ablation zone may be from about 7.5 mm to about 8.5 mm or from about 3 mm to about 12 mm. In some instances, the ablation profile of the central optical zone may be calculated using a Munnerlyn equation or a wavefront equation. Munnerlyn equations known in the art and well published. For example, Munnerlyn equations are discussed in Munnerlyn et al., "Photorefractive Keratectomy: A Technique For Laser Refractive Surgery," J. Cataract Refract. Surg. 14(1):46-52 (1998). Additional discussion of wavefront equations can be found in co-pending patent application entitled Direct Wavefront-Based Corneal Ablation Treatment Program, U.S. patent application Ser. No. 10/006,992, filed on Dec. 6, 2001, the full disclosure of which is herein incorporated by reference. Wavefront techniques are well adapted for use with advanced topographies, as described in U.S. Pat. Nos. 6,271,914 and 6,271,915, the full disclosures of which are incorporated herein by reference.

In a second aspect, the present invention provides a method for reprofiling a surface of a cornea of an eye by determining a maximum target depth of a first ablation profile, determining a maximum allowed ablation depth of the cornea, and treating the cornea with a depth reduced ablation profile when the maximum target depth of the first ablation profile is greater than the maximum allowed ablation depth of the cornea.

The method of the present invention may further include determining the first ablation profile in response to a size of an optical zone of the eye and an optical power correction. Treatment of the cornea with the depth reduced ablation profile can establish in the cornea an optically correct central optical zone and a blend zone peripheral to the central optical zone, wherein the blend zone may be at least partially within the optical zone of the eye. The optical power of the blend zone can gradually diminish with increasing radius from the central optical zone.

In a third aspect, the present invention may provide a system for reprofiling a surface of a cornea of an eye from an initial shape to a subsequent shape having correctively improved properties. The system can include a processor that generates an ablation profile having a blend region disposed peripherally to a central optical region, and may further include a laser system that directs laser energy onto the cornea according to the ablation profile, so as to reprofile a surface of the cornea from the initial shape to the subsequent shape. The ablation zone of the subsequent shape may have an optically correct central optical zone disposed in a central portion of the cornea, the central optical zone being formed by the central optical region of the ablation profile. The ablation zone also may have a blend zone disposed peripherally to the central optical zone and at least partially within an optical zone of the eye. The blend zone can have an optical power that gradually diminishes as a function of increasing radius from the central optical zone, and may be formed by the blend region of the ablation profile.

The processor of the present invention can comprise a simulated annealing module to generate the ablation profile, and the ablation profile approximates an ideal target shape. The simulated annealing module will often comprise data processing software and/or hardware, and may be integrated with other data processing structures. The area of the optical zone may be equal to a maximum pupil size of the eye. The blend zone provided by the present invention may have an optical power that gradually diminishes as a linear or nonlinear function of increasing radius out toward an ablation zone edge. The optical power of the blend zone gradually can diminish as a linear or nonlinear monotonic function of increasing radius out toward the optical zone edge, and the blend zone may terminate at an ablation zone edge.

The present invention may also include an ablation profile that includes a transition region disposed peripherally to the blend region, between an interface with the blend region and an ablation profile edge. Optionally, the transition region can be defined by a set of radially oriented cubic splines. A transition zone is effected by the transition region of the ablation profile. The maximum ablation depth of the ablation profile may be less than or equal to a maximum allowable ablation depth of the cornea.

The shape of the surface of the cornea may be reprofiled from an initial shape to a shape that mitigates myopia. The shape of the surface of the cornea may also be reprofiled from an initial shape to a shape that mitigates hyperopia, presbyopia, astigmatism, or irregular astigmatism. The dimension across the central optical zone may be from about 6 mm to about 7 mm, or from about 3 mm to about 9 mm.

In a fourth aspect, the present invention can provide a method for reprofiling a surface of a cornea of an eye by ablating a portion of the cornea to create an ablation zone that provides an ablation surface. The ablation zone may include an ablated central optical zone disposed in a central portion of the cornea, wherein the central optical zone provides an optically correct central optical surface. The optical zone may further include an ablated blend zone disposed peripherally to the ablated central optical zone and at least partially within an optical zone of the eye. Respectively, the optical zone may provide an optical surface, and the ablated blend zone may provide a blend surface. The blend surface can be disposed peripherally to the central optical surface and at least partially within the optical surface of the eye, and can have an optical power that gradually diminishes as a function of increasing radius out toward an ablation surface edge. Additionally, the ablation zone may also include a transition zone disposed peripherally to the blend zone, between an interface with the blend zone and an ablation zone edge. The transition zone can provide a transition surface, the transition surface being disposed peripherally to the blend surface and an ablation surface edge.

In a fifth aspect, the present invention may provide a method for reprofiling a surface of a cornea of an eye by determining an ablation profile having a central optical region, adding a blend region to the ablation profile to create a modified ablation profile. In this aspect, the blend region can be disposed peripherally to the central optical region. The method may further include treating the cornea with the modified ablation profile. Optionally, prior to the treatment step, the method may also include the step of adding a transition region to the modified ablation profile, the transition region being disposed peripherally to the blend region.

In addition to ablating human corneal tissue, the systems and methods of the present invention are well suited for ablating a wide variety of materials, such as plastic, polymethylacrylate (PMMA), porcine and bovine corneal tissue, and the like.

For a fuller understanding of the nature and advantages of the present invention, reference should be had to the ensuing detailed description taken in conjunction with the accompanying drawings.

DETAILED DESCRIPTION OF THE INVENTION

The present invention is particularly useful for enhancing the accuracy and efficacy of laser eye surgical procedures, such as photorefractive keratectomy (PRK), phototherapeutic keratectomy (PTK), laser in situ keratomileusis (LASIK), laser assisted epithelium keratomileusis (LASEK), and the like. Preferably, the present invention can provide enhanced refractive procedures by improving the methodology for deriving or generating a corneal ablation profile.

While the system and methods of the present invention are described primarily in the context of a laser eye surgery system, it should be understood that the techniques of the present invention may be adapted for use in alternative eye treatment procedures and systems such as radial keratotomy (e.g., by attenuating an incision depth at the periphery of a radial keratotomy incision), intraocular lenses, collagenous corneal tissue thermal remodeling, removable corneal lens structures, and the like.

According to the present invention, the region of the cornea to be ablated may be designated the ablation zone. Depending on the nature of the desired optical correction, the ablation zone may or may not be centered on the center of the pupil. A myopic condition may be treated, for example, by laser sculpting corneal tissue to reduce the curvature of the cornea. In contrast, a hyperopic condition may be treated by laser sculpting corneal tissue to steepen or increase the curvature, such as by providing an ablation profile having an ablation depth that increases with distance from the intended center of ablation. The result is a substantially spherical ablated shape for the cornea, of increased curvature, with a maximum depth of cut at the outer edge of the optically correct portion of the ablation zone. Cylindrical astigmatism, on the other hand, is typically treated by selectively removing corneal tissue according to a cylindrical ablation profile, in which the cylinder extends laterally across the optical axis of the eye. The optical zone of the cornea often corresponds to the area defined by a maximum pupil size of the eye, as when the pupil is fully and completely dilated.

The techniques of the present invention can be readily adapted for use with existing laser systems. By providing improved corneal ablation profiles for treating optical defects, the present invention may allow enhanced treatment of patients who have heretofore presented difficult or complicated treatment problems.

Figure 1:
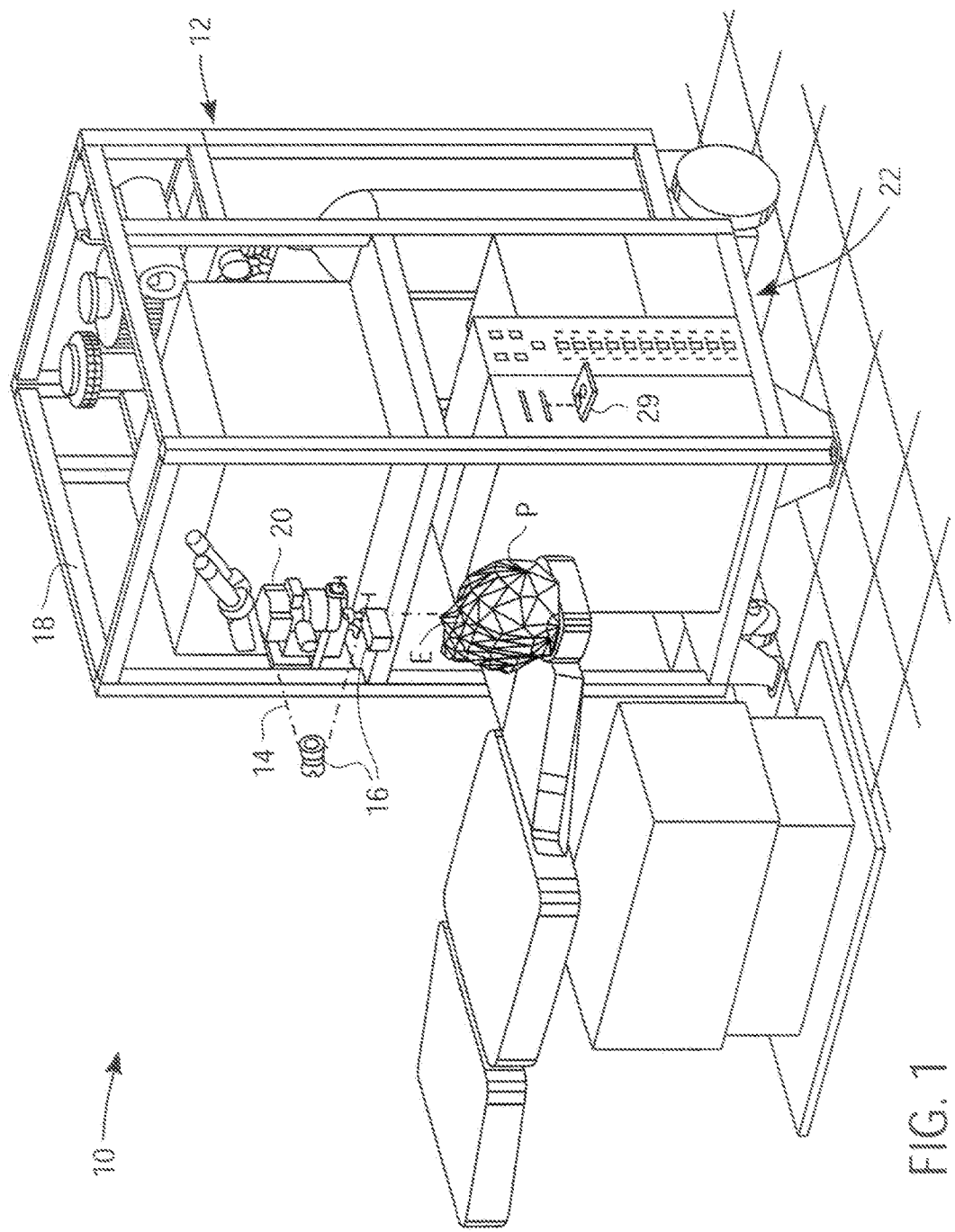
FIG. 1 is a schematic diagram of a laser surgery system for incorporating the present invention.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the conical tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention. As mentioned above, the systems and methods of the present invention are well suited for ablating a wide variety of materials, such as plastic, polymethylacrylate (PMMA), porcine and bovine corneal tissue, and the like.

As mentioned above, laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with a input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Basis data can be further characterized for particular lasers or operating conditions, by taking into account localized environmental variables such as temperature, humidity, airflow, and aspiration.

Figure 2:
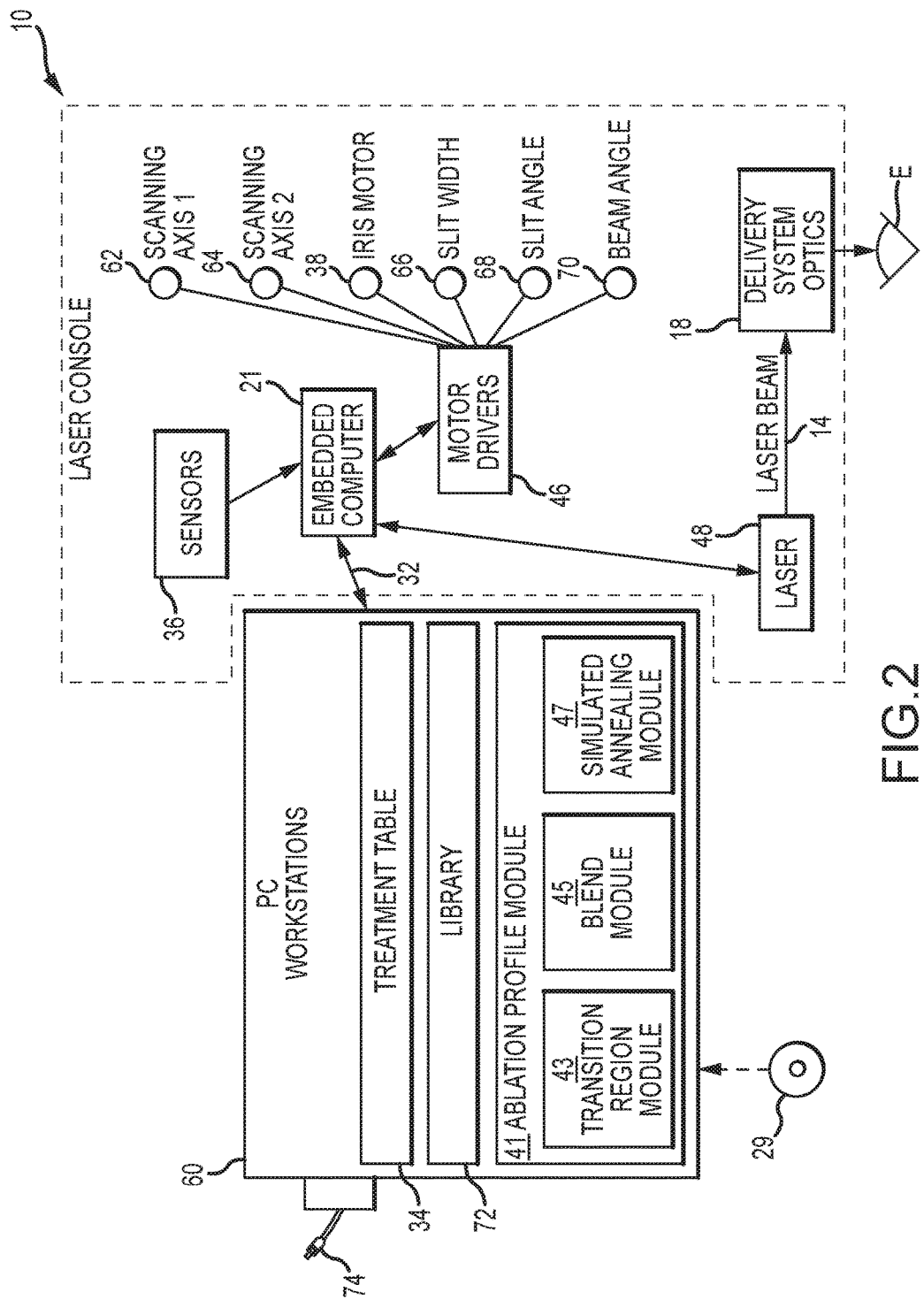
FIG. 2 is a block diagram of a laser surgery system for incorporating the present invention.

Referring now to FIG. 2, elements of an excimer laser system are shown. The subcomponents of laser surgery system 10 are known components and often comprise the elements of the VISX STAR™, VISX STAR S2™, or VISX STAR S3 ActiveTrak™ Excimer Laser Systems as commercially available from VISX, Incorporated of Sunnyvale, Calif.

A computer control system 60 enables precise control of laser system 10 to sculpt a surface shape specified in a laser treatment table 34. The controller 60, which generally comprises a PC workstation, makes use of a computer program stored on a tangible media 29 to generate treatment table 34. Alternatively, treatment table 34 is contained on tangible media 29, while the computer program that generates the treatment data is located externally. An embedded computer 21 within laser system 10 is in electronic communication with the PC workstation, and may thereby comprise a portion of the overall controller. Alternatively, a PC workstation may be embedded in the laser system and function as both the embedded computer and PC workstation for directing the ophthalmic surgery. The controller 60 further includes an ablation profile module 41, a transition region module 43, a blend module 45, and a simulated annealing module 47. The modules may comprise data processing software and/or hardware, and may be integrated with other data processing structures.

Embedded computer 21 is in electronic communication with a plurality of sensors 36 and a plurality of motor drivers 46. The motor drivers are coupled to the controller to vary the position and configuration of many of the optical components of the delivery optics 16 according to treatment table 34. For example, first and second scanning axis 62, 64 may control the position of the offset lens to move the laser beam over the surface of the cornea. Optionally, the laser beam may comprise several overlapping beamlets, as described in U.S. Pat. No. 6,331,177, the full disclosure of which is incorporated herein by reference. Iris motor 38 controls the diameter of the overall beam, and in some cases, the length of light transmitted through a variable width slit. Similarly slit width driver 66 controls the width of the variable slit. Slit angle driver 68 controls rotation of the slit about its axis. Beam angle driver 70 controls rotation of the beam, while excimer laser 48 is pulsed to generate the laser beam 14 after the various optical elements have been positioned to create a desired crater on eye E. Treatment table 34 may comprise a listing of all of the desired craters to be combined so as to effect a treatment therapy.

In addition, embedded computer 21 is couplable with the Excimer laser 48, such as an argon-fluorine laser with a 193 nanometer wavelength output designed to provide feedback stabilized fluence of 160 mJoules per square centimeter at the cornea at the patient's eye E via the deliver system optics generally designated with reference numeral 16.

Other lasers having a suitable wavelength may be used to make an ablative energy for removing a tissue from the eye. For example, solid state lasers such as a yttrium aluminum garnet (YAG) laser producing a fifth harmonic of a fundamental wavelength may be used to generate an ablative energy. Other ancillary components of the laser surgery system 10 which are not necessary to an understanding of the invention, such as a high resolution microscope, a video monitor for the microscope, a patient eye tracking system, and an ablation effluent evacuator/filter, as well as the gas delivery system, have been omitted to avoid prolixity.

Similarly, the keyboard, display, and conventional PC subsystem components (e.g., flexible/floppy and hard disk drives, memory boards and the like) have been omitted from the depiction of the PC work station 30. If desired, embedded computer 21 may be constructed with PC work station components and built into laser surgery system 10. In this case embedded computer 21 may supplant PC workstation 30.

For customizing ablations to treat irregular corneas, controller 60 will preferably include library 72 having a number of different photorefractive and/or phototherapeutic ablation profiles. Alternatively, library 72 may operate to generate the ablation profiles. These ablation profiles will often be used for treatment of spherical and/or cylindrical refractive errors of the eye by coaxially locating treatment center at the center of pupil P. To treat irregular corneas, these same ablation profiles may be directed to laterally offset treatment center using input device 74, as described, for example, in U.S. Pat. No. 6,245,059, the disclosure of which is incorporated herein by reference. Conveniently, the controller can modify the treatment table to offset the ablation profile by adjusting each ablation coordinate with the desired offset. Optionally, irregular corneal features may be treated with customized ablation profiles generated by wavefront techniques. A preferred method for solving for such ablation profiles is described below. Techniques for measuring corneal aberrations are described in U.S. Pat. Nos. 6,271,914 and 6,271,915, the full disclosures of which are incorporated herein by reference.

While the input device 74 is here schematically illustrated as a joystick, it should be understood that a variety of input mechanisms may be used. Suitable offset input mechanisms may include trackballs, touch screens, or a wide variety of alternative pointing devices. Still further alternative input mechanisms include keypads, data transmission mechanisms such as an ethernet, intranet, internet, a modem, or the like. These or other input mechanisms may be used to identify an offset treatment center which is offset laterally from the center of the pupil of the eye.

Figure 3:
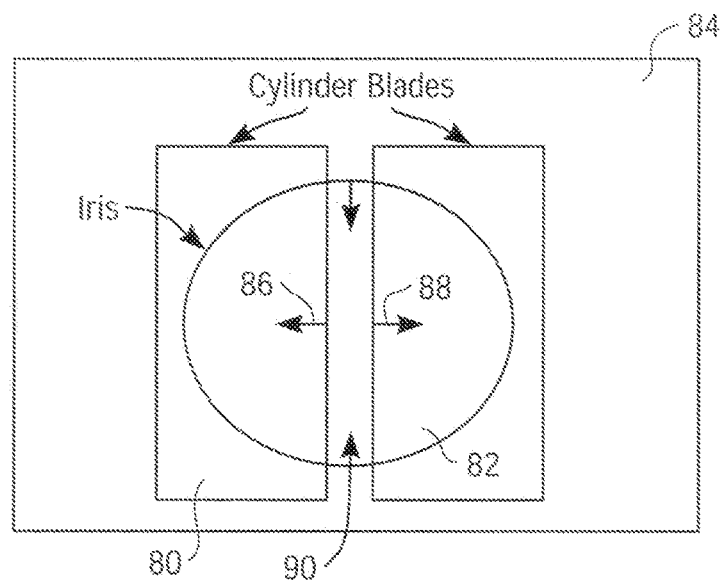
FIG. 3 is a schematic plan view illustrating a movable slit and variable aperture used in the laser system.

The iris motor 38 is used to control the diameter of a variable diameter iris schematically depicted in FIG. 3. The astigmatism motor 66 is used to control the separation distance between a pair of cylinder blades 80, 82 which are mounted on a platform 84 for bi-directional translational motion in the direction of arrows 86, 88. Platform 84 is rotatably mounted on a second platform (not illustrated) and is rotationally driven by astigmatism angle motor 68 in a conventional way in order to enable alignment of the slit axis (illustrated in a vertical orientation in FIG. 3) with the appropriate coordinate axes of the patient's eye. Iris 90 is driven by iris motor 38 in a known way to change the diameter of the iris opening from a fully opened position (the position illustrated in FIG. 3) to a fully closed position in which the aperture is closed to a minimum diameter of 0.8 mm. It is understood that the variable diameter iris 90 and the cylinder blades 80, 82 are positioned with respect to the output of laser 48 in such a manner as to intercept the beam prior to irradiation of the corneal surface of the patient's eye E. For the purpose of this application, it may be assumed that iris 90 and cylinder blades 80, 82 are part or the delivery system optics subunit 16 shown in FIG. 2.

The system of FIGS. 1-3 is used according to the invention to provide presbyopic, hyperopic, myopic, astigmatic, and other error treatments to the surface of the cornea by incorporating blend regions, depth reduction, or transition regions into laser ablation profiles. Other techniques besides the above may be used to generate the ablation profile as desired for a particular patient or treatment. For example, a lens may be used to profile a laser beam exiting from an aperture by focusing the beam to a suitably small area and desired energy profile as described in U.S. Pat. No. 4,718,418, the full disclosure of which is herein incorporated by reference. Also a diffractive optic may be used to adjust an energy profile of the laser beam on the surface of the eye as described in co-pending application entitled Laser Delivery System and Method with Diffractive Optic Beam Integration, U.S. patent application Ser. No. 09/015,841 filed on Jan. 29, 1998 the full disclosure of which is herein incorporated by reference.

Depth Reduction and Blend Zones

Figure 4:
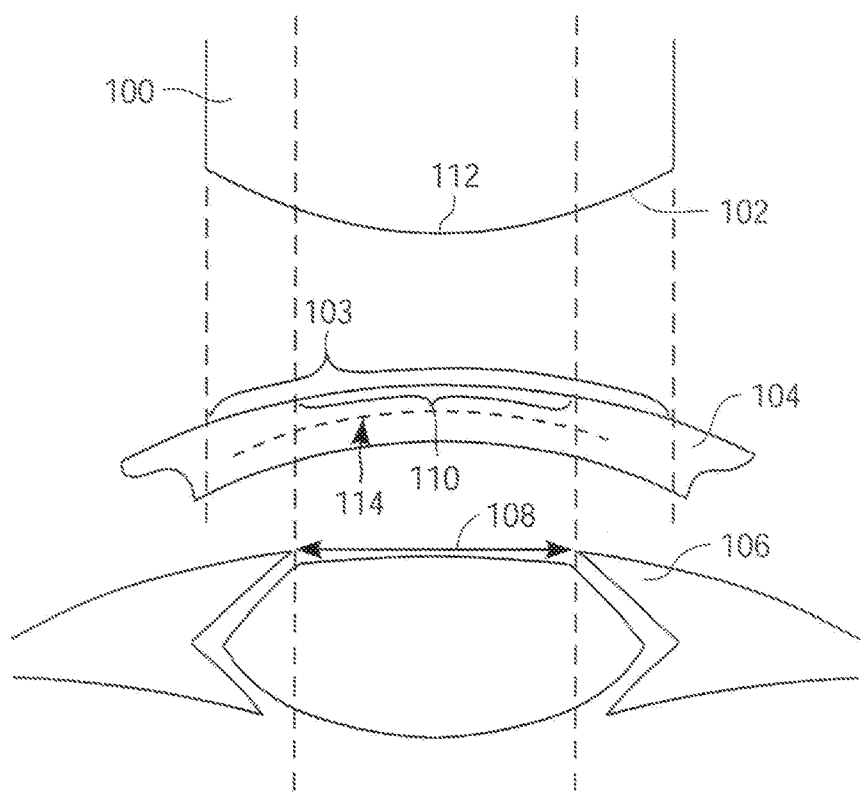
FIG. 4 schematically illustrates an ablation profile for treating the cornea.

A schematic illustration of a laser ablation treatment is shown in FIG. 4. Laser ablation treatment 100 provides a laser Ablation profile 102 that ablates a corresponding ablation zone 103 of the cornea 104, and thereby reshapes the cornea. The iris 106 of the eye, when fully dilated, defines the maximum pupil size 108. The optical zone 110 is that portion of the cornea 104 corresponding to the maximum pupil size. Relatedly, the optical region 112 is that portion of the ablation profile 102 corresponding to the maximum pupil size 108. The maximum allowed ablation depth for the cornea is 114.

Figure 5A:
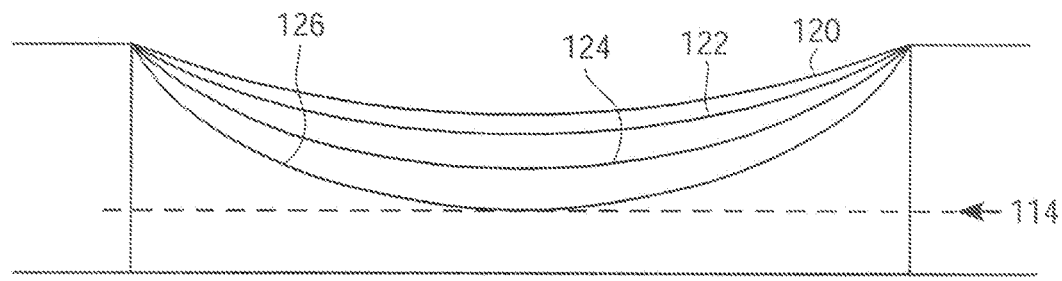
FIGS. 5A-5D illustrate ablation profiles for treating the cornea (myopia).
Figure 5B:
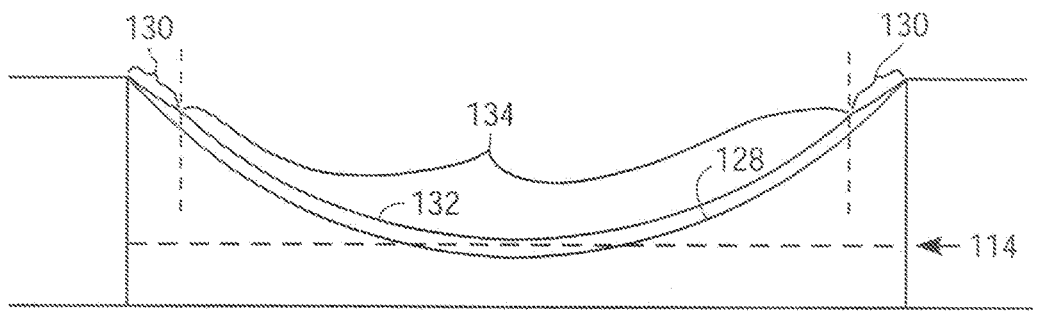

A representative illustration of a series of ablation profiles for treating myopia is shown in FIG. 5A. In laser treatments for myopia, the intent is to reduce the curvature, and thus the optical power, of the cornea. Accordingly, ablation profiles 120, 122, and 124 confer progressively greater reductions in the optical power of the cornea, by providing progressively deeper ablations into the corneal tissue. As the curvature of the ablation is sharpened, the optical power of the cornea is progressively decreased. It is the curvature of the cornea that determines the optical power. Again, maximum allowed ablation depth 114 is the depth beyond which ablation may be unsafe or otherwise undesired, and so an ablation as deep as ablation profile 126 is acceptable. In some cases, a stronger treatment or optical correction may be advantageous. The deeper ablation profile 128 shown in FIG. 5B represents the desired stronger treatment, yet because of its excessive depth, the ablation may be unsafe. However, by incorporating a blend region 130 into ablation profile 132, it is possible to achieve a treatment equally as strong as ablation profile 128, yet not ablate beyond the maximum allowed ablation depth 114. The portion of the depth reduced ablation profile 132 central to the blend region 130 is the central optical region 134. The blend region is formulated by the blend region module.

Figure 5C:
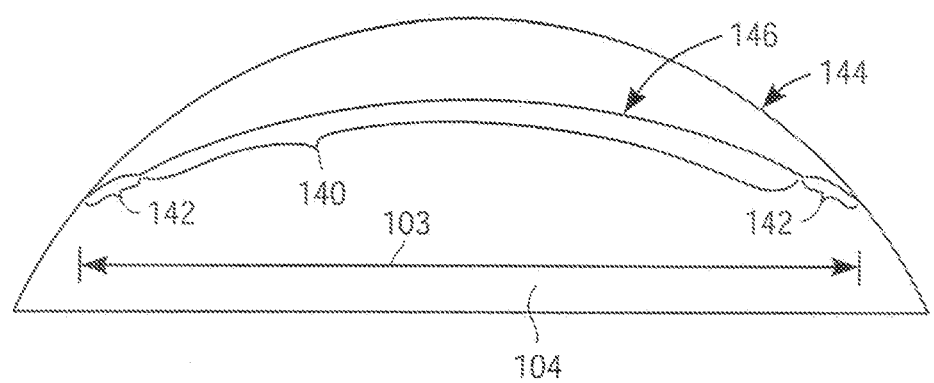

FIG. 5C further illustrates the concept that treatment with any ablation profile creates a corresponding ablation zone 103 in the cornea 104. Accordingly, depth reduced ablation profile 132 creates an ablation zone 103 that includes an optically correct central optical zone 140 (corresponding to the central optical region 134), and a blend zone 142 (corresponding to blend region 130), wherein the blend zone 142 is disposed peripherally to the central optical zone 140, and has an optical power that gradually diminishes with increasing radius from the central optical zone 140. In accordance with a general myopia treatment, the original contour 144 of the cornea has been modified to a lower powered ablated contour 146.

Figure 5D:
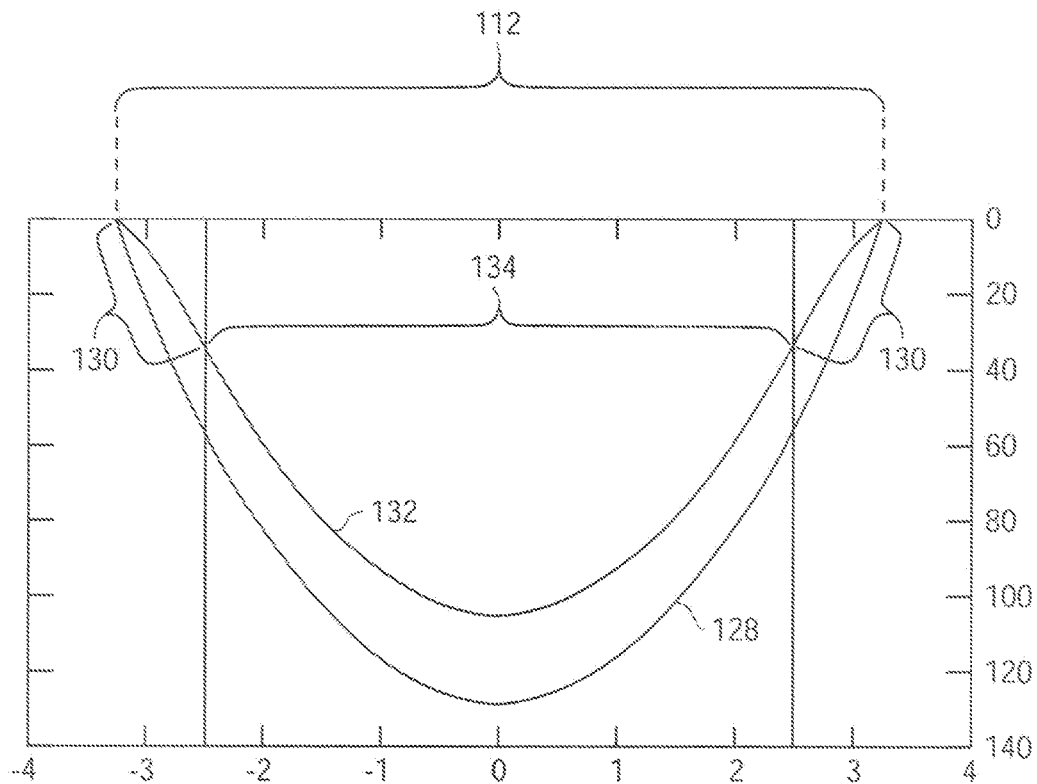

FIG. 5D illustrates a particular depth reduced ablation profile according to the principles of the present invention. Analogous to FIG. 5C, deeper ablation profile 128 reaches a maximum depth of approximately 130 μm. In some cases, this maximum depth may exceed a maximum allowed ablation depth for a particular cornea. In order to reduce the maximum depth attic deeper ablation profile 128 to a more acceptable depth of 105 µm, and still retain the same optical power provided by the deeper ablation profile 128, a peripherally disposed blend region 130 is introduced. With the application of the blend region 130, it is possible to formulate the depth reduced ablation profile 132. As the figure illustrates, both the deeper ablation profile 128 and the depth reduced ablation profile 132 exhibit an optical region 112 diameter of approximately 6.5 mm. As shown, the central optical region 134 of the depth reduced ablation profile 132 is approximately 5 mm in diameter, however the ablation profile may be formulated to provide central optical regions 134 of varying sizes. In some cases, the central optical region 134 may range from about 6 mm to about 7 mm in diameter. In other cases, the central optical region 134 may range from about 3 mm to about 3 mm to about 9 mm in diameter.

Figure 6:
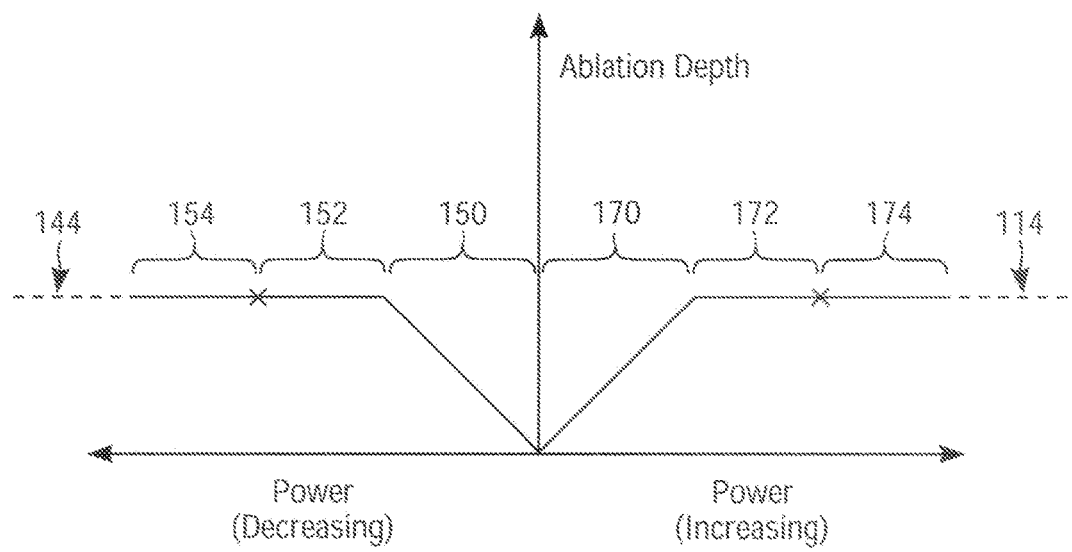
FIG. 6 illustrates the relationship between ablation depth and corneal optical power in myopia and hyperopia treatments.

A representative graph illustrating a relationship between optical power of the eye and maximum ablation depth is shown in FIG. 6. The left side of the graph is divided into three sections: regular myopia ablation profile section 150, depth adjusted myopia profile section 152, and invalid myopia refraction section 154. The horizontal axis represents the optical power of the cornea, and the vertical axis represents the depth of any given ablation profile.

The first section 150 demonstrates the principle that, in a series of ablation profiles for myopia (as shown in FIG. 5A), the optical power of the cornea decreases as the depth of the ablation profile increases. This correlation continues until the depth of the ablation profile reaches a maximum allowed ablation depth 114. Any ablation profile in this section is not depth adjusted. In a presently preferred embodiment, the maximum allowed ablation depth is determined by subtracting the minimum residual stroma from the stromal bed depth.

The second section 152 demonstrates the principle of depth reduction discussed above with respect to FIG. 5B. Here, the maximum ablation depth of a standard ablation profile for the desired correction would exceed the maximum allowed ablation depth of the cornea. In order to provide an ablation profile of reduced depth relative to the desired standard ablation profile, yet still achieve a decrease in optical power in the cornea, the ablation profile is modified by decreasing the size of the central optical region, and introducing a peripherally disposed blend region. In a preferred embodiment, the decrease in corneal optical power comes from ablation profiles having central optical regions with progressively sharper curvatures. Often, this will be accompanied by blend regions of increasingly larger area.

With a very high power correction, or in a patient presenting a large optical zone or maximum pupil size, the corrective ablation profile may have an optical region that is smaller than the optical zone. For example, if the size of the central optical region is very small, it may not be possible to incorporate a refractively acceptable blend region into the ablation profile and still provide an optical region that would span the area of the optical zone of the cornea. This situation is represented in section 154 of the graph.

Figure 5E:
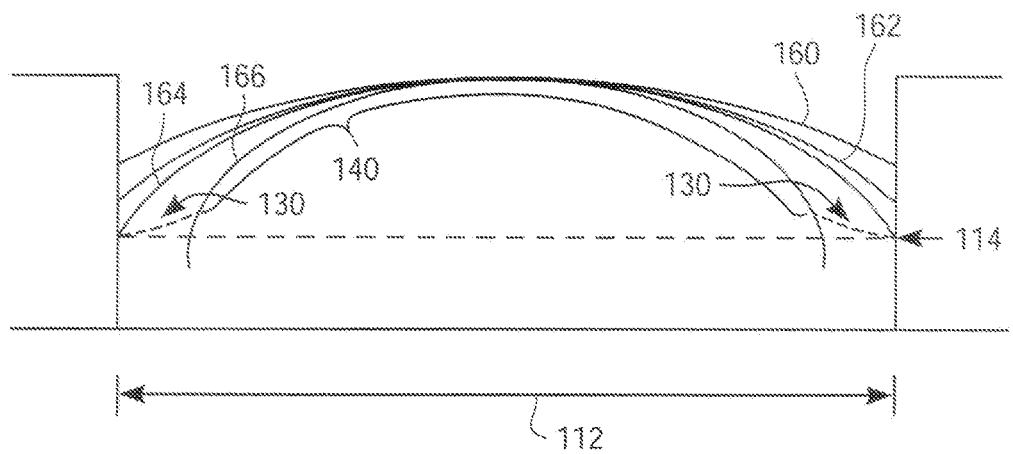
FIG. 5E illustrates an ablation profile for treating the cornea (hyperopia).

FIG. 5E illustrates many of these same principles in the application of hyperopia treatments. In laser treatments for hyperopia, the intent is to increase the curvature, and thus the optical power, of the cornea. Accordingly, ablation profiles 160 and 162 confer progressively greater increases in the optical power of the cornea, by providing progressively deeper ablations into the corneal tissue. Once more, maximum allowed ablation depth 114 provides a limit beyond which ablation may be unwanted. Thus, an ablation profile as deep as ablation profile 164 is acceptable. In some cases, a stronger treatment or optical correction may be advantageous. The deeper ablation profile 166 represents the desired stronger treatment, yet because of its excessive depth, the ablation may be unsafe. However, by incorporating a blend region 130 into ablation profile 166, it is possible to achieve a treatment with the corrective strength of ablation profile 166, yet not ablate beyond the maximum allowed ablation depth 114. As before, the optical region 112 of the ablation profile is then defined by the central optical region 134 and the blend zone 130.

A representative graph illustrating a relationship between optical power of the cornea and maximum ablation depth in hyperopia is also shown in FIG. 6. The right side of the graph is divided into three sections: regular hyperopia ablation profile 170, depth adjusted hyperopia ablation profile 172, and invalid hyperopia refraction 174. The horizontal axis represents the optical power of the cornea, and the vertical axis represents the depth of any given ablation profile.

Section 170 demonstrates the principle that, in a series of ablation profiles for hyperopia (shown as ablation profiles 160 and 164 in FIG. 5E), the optical power of the cornea increases as the depth of the ablation profile increases. This correlation continues until the depth of the ablation profile reaches a maximum allowed ablation depth. Any ablation profile in this section is not depth adjusted, because the maximum ablation depth is less than the maximum allowed ablation depth 114. Section 172 explains the circumstance when the maximum ablation depth of an ablation profile for a desired optical correction is greater than the maximum allowed ablation depth for the cornea.

In order to provide an ablation profile of reduced depth relative to the desired ablation profile, yet still achieve an increase in optical power of the cornea, the ablation profile is modified by introducing a peripherally disposed blend region and decreasing the size of the central optical region. In a preferred embodiment, the increase in corneal power comes from ablation profiles having central optical regions with progressively sharper curvatures. Often, this will be accompanied by blend regions of increasingly larger size.

With a very high power correction, or in a patient presenting a large optically functional region, the corrective ablation profile may have an optical zone that is smaller than the optically functional region. For example, if the size of the central optical zone is very small, it may not be possible to incorporate a refractively acceptable blend zone and still provide an optical zone that would span the area of the optically functional region. This situation is represented in section 174.

Figure 7:
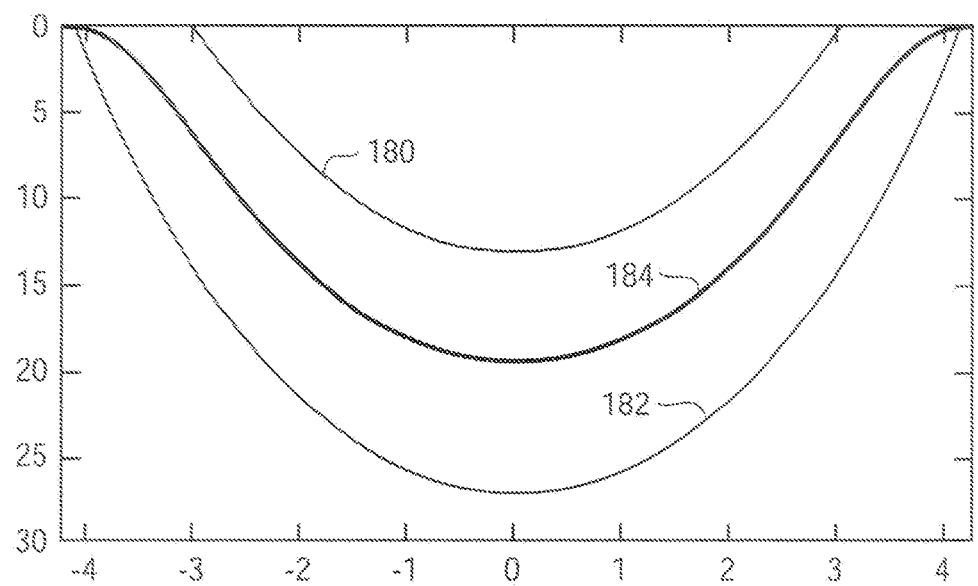
FIGS. 7 and 8 schematically illustrates ablation profiles for treating the cornea.
Figure 8:
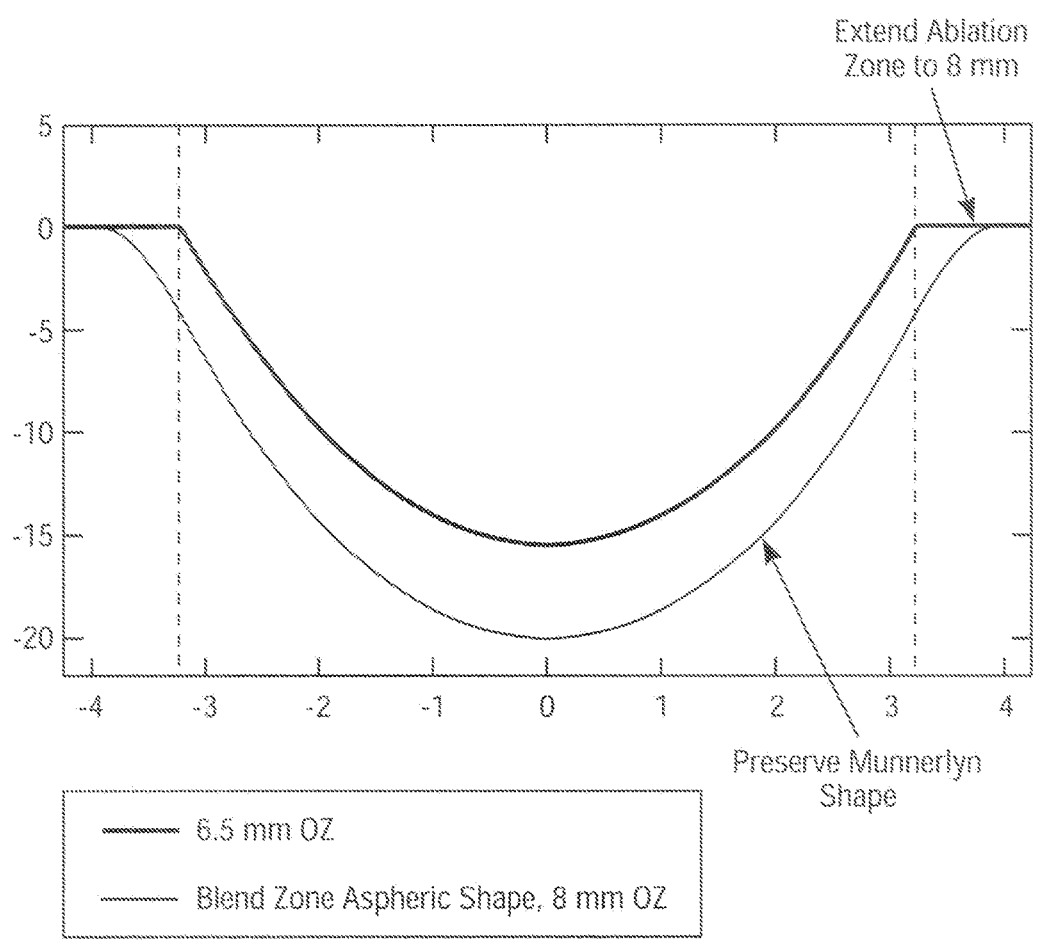

Another illustrative plot of the application of a blend region into an ablation profile for myopia treatment is shown in FIG. 7. Ablation profile 180 represents a standard Munnerlyn shape of 6.5 mm diameter. For a patient having a large optical zone (e.g. 8 mm diameter), it may be preferable to treat the patient with an ablation profile that covers the entire 8 mm optical zone. This is accomplished by adding a blend region to the standard 6.5 mm ablation profile 180. In order to do so, a standard 8 mm Munnerlyn ablation profile 182 is calculated. A constant depth is then subtracted from ablation profile 182 inside the 6.5 mm central, optical region, and a transform is applied to the shape at the blend region, between 6.5 mm and 8 mm. The result is ablation profile 184. In effect, this represents the addition of a blend region to a 6.5 mm optical region ablation profile, resulting in an aspheric ablation profile 184 having a deeper, blended 8 mm optical region. This approach is also illustrated in FIG. 8, effectively achieving the optical zone size of the standard 8 mm ablation profile, but minimizing the ablation depth required to do so.

Characteristics of the resulting blend zone include: a precise mathematically defined relation to standard ablation shape; an optical power that changes smoothly as a function of radius; and flexibly defined parameters, in that the extent and amount of optical power change are specifiable.

Transition Zone

The function of the transition region is to bring the ablation depth smoothly to zero depth at the ablation profile edge. The transition zone is general in nature, and is well suited for implementation in a wide variety of ablation profiles, including arbitrary wavefront shapes. Whether a transition zone is needed or desirable often depends on the shape of the target ablation profile. For instance, treatment of mild spherical myopia involves an ablation profile which gradually tapers at its periphery, so that no transition zone may be needed.

In contrast, treatments for astigmatism involve a cylindrical ablation profile that would otherwise have abrupt axial ends. To avoid such discontinuities in the ablated surface, the apertures of the present invention may be varied, per the programming of the system controller, to impose a smooth astigmatism transition zone between the optical zone and the surrounding corneal surface. Generally, the shape of the transition zone applied by the present invention during a given treatment is based on the ablation profile.

For forming the optical zone during hyperopic corrections, the variable width slit and variable diameter iris define an elongate rectangular beam. The rectangular beam is rotated about an ablation center with a major edge of the beam following a series of circumferential bands or arcs. A transition zone shape is generated by the outer edge of the rectangular beam as the inner edge rotates along an arc within the optical zone. Hence, the shape of the transition zone during a hyperopic refraction correcting procedure is an artifact of the mechanical arrangement used to define the optical zone.

Still further transition zones shapes are generated by the method and systems of the present invention for other specific ablation shapes. For example, the refractive treatment used to correct for hyperopic astigmatism is ablation of a centrally steepening cylindrical shape from the optical zone. Absent any transition zone, the edges of the optical zone might comprise abrupt changes in ablation depth. As such discontinuities are generally avoided, the present invention imposes gradually tapering ablation depths beyond the optical zone.

Figure 9A:
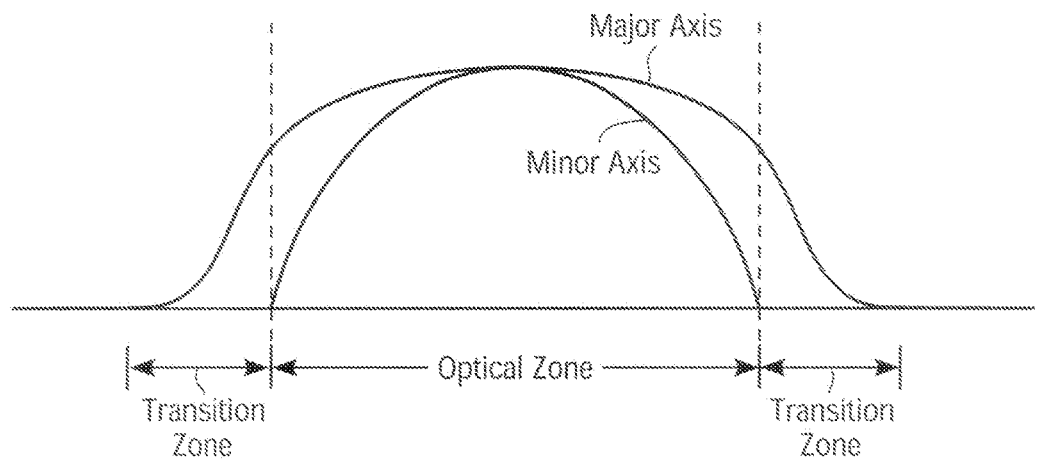
FIGS. 9A, 9B, 10A, and 10B schematically illustrate transition zones according to the present invention.
Figure 9B:
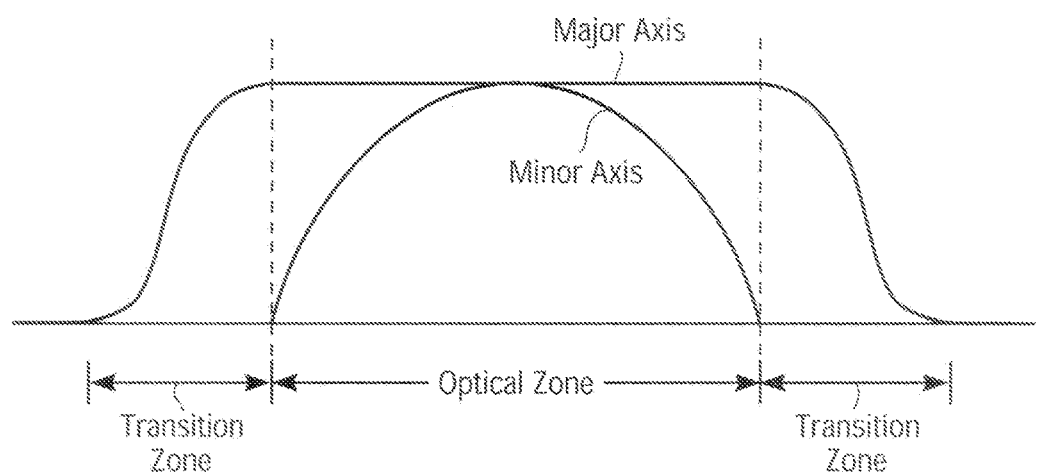
Figure 10A:
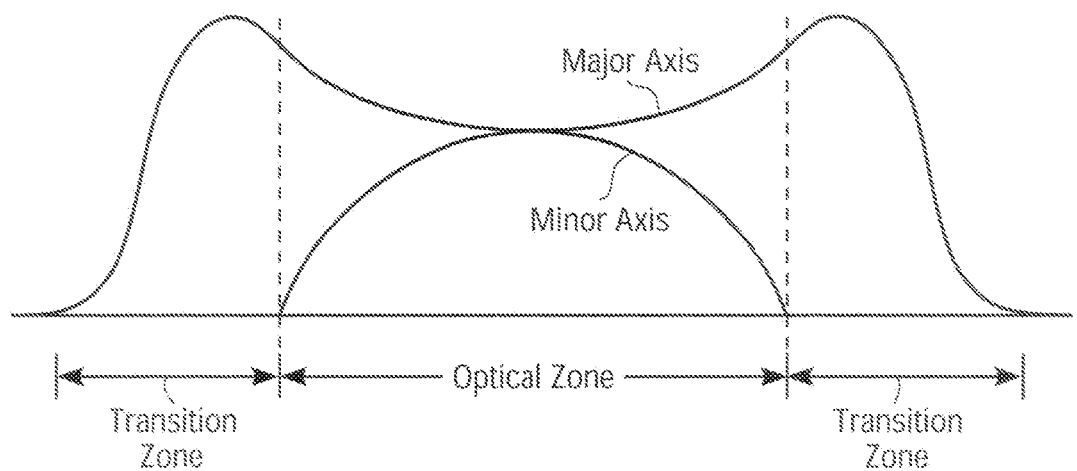
Figure 10B:
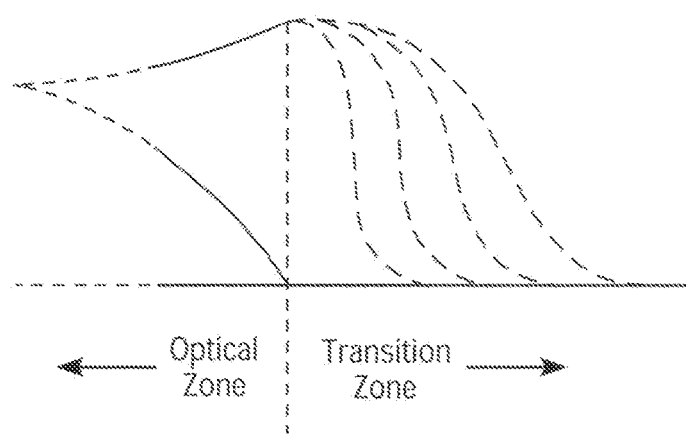

As an illustrative example, FIG. 9A shows a myopic treatment with astigmatism having a transition zone on the major axis, but not on the minor axis. Relatedly, FIG. 9B shows a cylinder having a transition zone on the major axis but not on the minor axis. This shape has a larger transition zone than shown in FIG. 9A. In another example, FIG. 10A represents a mixed astigmatism treatment shape, having an even larger transition zone. As shown in FIG. 10B, the size of the transition zone is adjustable, and the transition zone can be made as gentle as desired.

In one embodiment of the present invention, the transition region module produces the transition region shapes in a series of steps. First, the proper optical region shape is determined, either by Munnerlyn equations or wavefront techniques. Second, a blend region may optionally be applied. Third, the depth and radial slope of the ablation shape at the outer edge of the optical region, or at the blend region if present, is calculated. Fourth, a cubic spline is used to connect the outer edge of the optical region, or the blend region, to the ablation profile edge. Alternatively, in the case of the wavefront transition region, the transition region may be smoothed by pixel averaging, or by spatial averaging of depth.

Once the desired ablation shape has been determined, a next step is to define the parameters of the actual laser ablation required to administer the treatment ablation profile. A particularly useful way of determining these parameters is by using an ablation equation, such as the one shown below.

$$AblationShape = \sum_{n=1}^{TotalPulses} (PulseShape_n \otimes Position_n)$$

Essentially, this equation is based on the principle that a treatment ablation is the sum of each of the individual laser pulses. This equation has been empirically verified on a variety of materials including plastic, and bovine, porcine, and human corneal tissue.

In this equation, the AblationShape variable represents the desired ablation shape. In this sense, it is a known variable. The target shape can be, for example, a simple sphere, an ellipse, a cylinder for treating myopia or hyperopia, or even a saddle for treating mixed astigmatism. The target shape can be any arbitrary shape, such as the map from a wavefront type device or any other topography system. What is more, the target shape can contain, for example, a blend zone or a reduced depth profile. Further, the AblationShape may or may not include a transition zone.

Figure 11:
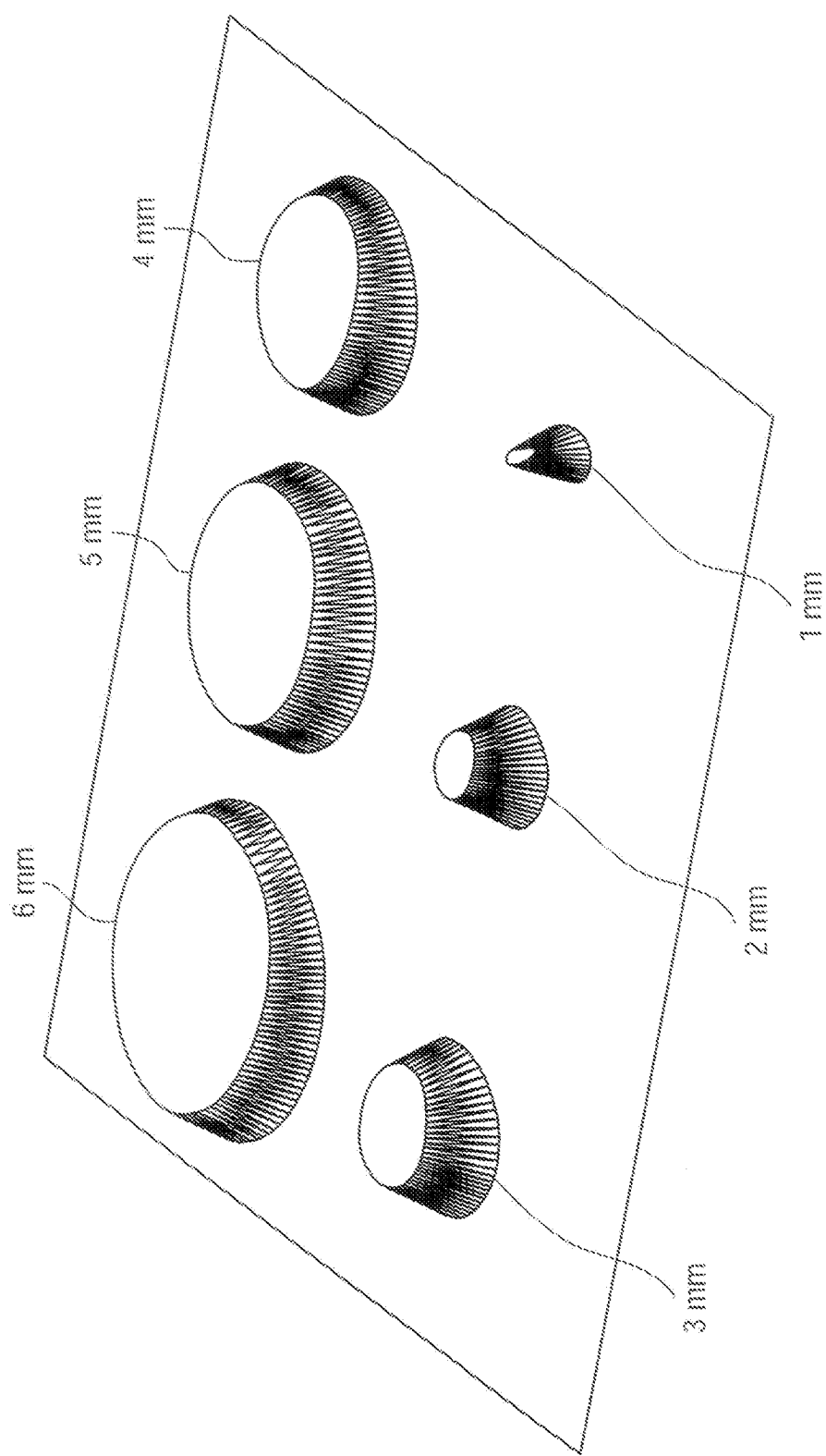
FIG. 11 schematically illustrates corneal ablation data for a series of laser pulses.

The PulseShape variable, which is also a known variable, represents the ablation shape of each laser pulse size to be used. The PulseShape typically varies for different ablated materials, such as plastic, animal cornea, or human cornea. The PulseShape also typically varies for each laser pulse diameter. An example of this type of ablation data is shown in FIG. 11. This figure shows different shapes of craters expected from a single laser pulse. There is a unique description for every unique pulse shape or size to be used. By systematically measuring the shape which each laser pulse ablates onto a specific target material, it is possible to generate such basis data for a variety of materials, such as tissue or plastic. For a given material, at a given diameter, the shape is generally consistent from laser system to laser system.

A fixed spot laser may have only one description, while a variable spot laser could have as many as desired. There is no requirement that the crater shape be flat, round, or symmetric. As long as it can be described mathematically or with an array of data, it can be incorporated in the equation.

In order to create the ablated surface, it is useful to determine the locations where each of the laser pulses will be applied. The Position variable, which represents the exact position of every laser pulse, is an unknown variable. This variable is calculated by solving the ablation equation. Put another way, the output is a set of instructions for creating the target ablation shape using the laser pulses. This is sometimes called a treatment table. The treatment table consists of a list of individual pulses, each containing the size and offset, or position, to be used for that pulse. When the laser tires according to the instructions in the treatment table, the target shape will be created.

The target ablation shape is a theoretical construct; it is a mathematically perfect representation of a desired ablation outcome. Put another way, while the application of thousands of specifically placed brief laser pulses can create an actual ablation shape that approaches the ideal target ablation shape, in the end it is still an approximation thereof.

Therefore, solving for the Position variable can allow for the formulation of a corresponding ablation shape that approaches the target ablation shape as closely as possible. In this way each of the thousands of pulse positions are individually determined so as to minimize the difference between the ideal target ablation shape and the actual resulting ablation shape. In a system for ablating tissue using a scanning laser, a presently preferred computational technique for achieving this goal employs simulated annealing.

Other mathematical approaches include, for example, the SALSA Algorithm. SALSA is an acronym for Simulated Annealing Least Squares Algorithm. It is an algorithm that solves an equation having over 10,000 unknowns. The algorithm finds the best solution by selecting: the number of pulses, the size of each pulse, and the location of each pulse. It is an exact algorithm, and makes no statistical assumptions.

Simulated Annealing is a recent, proven method to solve otherwise intractable problems, and may be used to solve the ablation equation discussed above. This is more fully described in PCT Application No. PCT/US01/08337, filed Mar. 14, 2001, the entire disclose of which is incorporated herein by reference. Sec also W. H. Press et al., "Numerical Recipes in C" $2^{nd}$ Ed., Cambridge University Press, pp. 444-455 (1992). This approach is also further discussed in co-pending U.S. patent application Ser. No. 09/805,737, the entire disclosure of which is incorporated herein by reference.

Simulated annealing is a method used for minimizing (or maximizing) the parameters of a function. It is particularly suited to problems with very large, poorly behaved function spaces. Simulated annealing can be applied in the same way regardless of how many dimensions are present in the search space. It can be used to optimize any conditions that can be expressed numerically, and it does not require a derivative. It can also provide an accurate overall minimum despite local minima in the search space, for example.

While the above provides a full and complete disclosure of the preferred embodiments of the present invention, various modifications, alternate constructions and equivalents may be employed as desired. Therefore, the above description and illustrations should not be construed as limiting the invention, which is defined by the appended claims.

What is claimed is:

1. A method for reprofiling a surface of a cornea of an eye, the method comprising:
    determining a first ablation profile based on an area of an optical zone of the eye and an optical power correction;
    determining a maximum target depth of the first ablation profile;
    determining a maximum allowed ablation depth of the cornea;
    determining that the maximum target depth of the first ablation profile is greater than the maximum allowed ablation depth of the cornea;
    executing, with a processor, a machine readable code embodied on a non-transitory tangible medium, wherein execution of the code causes the processor to determine a depth reduced ablation profile in response to the determination that the maximum target depth of the first ablation profile is greater than the maximum allowed ablation depth of the cornea, and wherein the depth reduced ablation profile has an ablation depth less than the maximum allowed ablation depth of the cornea; and
    treating the cornea with the depth reduced ablation profile,
    wherein treatment of the cornea with the depth reduced ablation profile establishes in the cornea an ablation zone having an optically correct central optical zone and a blend zone peripheral to the central optical zone, the blend zone at least partially within the optical zone of the eye and having an optical power that changes as a linear function of increasing radius from the central optical zone, and wherein the area of the optical zone of the eye is equal to a maximum possible pupil size of the eye.

2. The method according to claim 1, wherein the ablation zone further comprises a transition zone disposed peripherally to the blend zone, the transition zone being defined by a set of radially oriented cubic splines.

3. The method according to claim 1, wherein a subsequent shape of the surface of the cornea following treatment of the cornea with the depth reduced ablation profile mitigates myopia, hyperopia, presbyopia, astigmatism, or irregular astigmatism.

4. The method according to claim 1, wherein a dimension across the central optical zone is from 6 mm to 7 mm.

5. The method according to claim 1, wherein a dimension across the ablation zone is from 7.5 mm to 8.5 mm.

6. The method according to claim 1, wherein the blend zone terminates at an ablation zone edge.

7. The method according to claim 1, wherein the optical zone is within a range from 6 mm to 8 mm in diameter and the central optical zone is within a range from 5 mm to 7 mm in diameter.

8. The method according to claim 1, wherein the ablation profile is generated so that the central optical zone corresponds to a Munnerlyn equation or a wavefront equation.

9. A system for reprofiling a surface of a cornea of an eye of a patient from an initial shape to a subsequent shape, the system comprising:
    a processor comprising a non-transitory tangible medium embodying machine readable code that generates an ablation profile; and
    a laser system that directs laser energy onto the cornea according to the ablation profile so as to reprofile a surface of the cornea from the initial shape to the subsequent shape, an ablation zone of the subsequent shape comprising:
    an optically correct central optical zone disposed in a central portion of the cornea;
    an ablation zone edge disposed peripherally to an optical zone of the ablation zone, the optical zone corresponding to the maximum pupil size of the eye of the patient;
    a blend zone disposed peripherally to the central optical zone and partially within the optical zone, the blend zone having an optical power that changes as a linear function of increasing radius from the central optical zone.

10. The system according to claim 9, wherein the ablation zone further comprises a transition zone disposed peripherally to the blend zone, the transition zone being defined by a set of radially oriented cubic splines.

11. The system according to claim 9, wherein the subsequent shape of the surface of the cornea mitigates myopia.

12. The system according to claim 9, wherein the subsequent shape of the surface of the cornea mitigates hyperopia, presbyopia, astigmatism, or irregular astigmatism.

13. The system according to claim 9, wherein a dimension across the central optical zone is from 6 mm to 7 mm.

14. The system according to claim 9, wherein a dimension across the ablation zone is from 7.5 mm to 8.5 mm.

15. The system according to claim 9, wherein the blend zone terminates at the ablation zone edge.

16. The system according to claim 9, wherein the optical zone is within a range from 6 mm to 8 mm in diameter.

17. The system according to claim 9, wherein the central optical zone is within a range from 5 mm to 7 mm in diameter.

18. The system according to claim 9, wherein the ablation profile is generated so that the central optical zone corresponds to a Munnerlyn equation or a wavefront equation.

* * * * *